United States Patent [19]
Kim et al.

[11] Patent Number: 5,460,960
[45] Date of Patent: Oct. 24, 1995

[54] PRODUCTION OF IMMUNOPROXIMITY CATALYSTS

[75] Inventors: Peter S. Kim, Brookline, Mass.; Neville R. Kallenbach, New York, N.Y.

[73] Assignee: IGEN, Inc., Gaithersburg, Md.

[21] Appl. No.: 187,810

[22] Filed: Jan. 27, 1994

Related U.S. Application Data

[63] Continuation of Ser. No. 857,683, Mar. 25, 1992, abandoned, which is a continuation of Ser. No. 92,230, Sep. 2, 1987, abandoned.

[51] Int. Cl.$^6$ ............................................. C12N 9/00
[52] U.S. Cl. ............... 435/188.5; 435/183; 435/240.27; 530/388.9; 530/389.8
[58] Field of Search ...................... 435/240.27, 188.5, 435/183, 195; 530/388.9, 389.8

[56] References Cited

U.S. PATENT DOCUMENTS

| | | | |
|---|---|---|---|
| 4,196,265 | 5/1980 | Koprowski et al. | 435/2 |
| 4,376,110 | 3/1983 | David et al. | 436/513 |
| 4,492,751 | 1/1985 | Boguslaski et al. | 435/7 |
| 4,493,890 | 1/1985 | Morris | 435/7 |
| 4,659,567 | 4/1987 | Tramontano et al. | 424/85 |
| 4,792,446 | 12/1988 | Kim et al. | 424/85.8 |
| 4,888,281 | 12/1989 | Schochectman et al. | 435/72 |
| 4,900,674 | 2/1990 | Benkovic et al. | 435/232 |

FOREIGN PATENT DOCUMENTS

| | | |
|---|---|---|
| 0260939 | 3/1988 | European Pat. Off. . |
| 2193964 | 2/1988 | United Kingdom . |
| WO85/02414 | 6/1985 | WIPO . |

OTHER PUBLICATIONS

Fessenden, R. & Fessenden J., *Organic Chemistry* 511 (1980).
Streitwiesser, et al., *Introduction to Organic Chemistry*, 349 (1976).
*CRC Handbook of Chemistry and Physics*, Weast, R. C., Editor (63rd Edition, CRC Press, Inc., Boca Raton, Fla.) (1982–1983), p. F–82.
*The Concise Chemical and Technical Dictionary*, Bennett, H., Editor (Second Enlarged Edition, Chemical Publishing Co., Inc., New York, N.Y.) (1962), pp. 185–186.
Erhan, S. and Greller, L. D., *Nature*, vol. 251, 353 (1974).
Lerner, R. A., Benkovic, S. J., Schultz, P. G. "At the Crossroads of Chemistry and Immunology: Catalytic Antibodies" Science 252: 659–667 (3 May 1991).
Pollack, S. J., Nakayama, G. R., and Schultz, P. G. "Introduction of Nucleophiles and Spectroscopic Probes into Antibody Combining Sites." *Science* 242: 1038–1040 (18 Nov. 1988).
Pollack, S. J. and Schultz, P. G. "A Semisynthetic Antibody" J. Am. Chem. Soc. 111, 1747–1748 (1989).
Napper, A. D. et al., "A Stereospecific Cyclization Catalyzed By An Antibody", *Science*, 237, 1041–1043 (28 Aug. 1987).
Tramontano, A. et al., "Catalytic Antibodies", *Science*, 234, 1566–1570 (1986).
Pauling, L., *Nature*, 161, 707, (1948).
Pollack, S. J., Jacobs, J. W., Schultz, P. G., *Science* 234, 1570 (1986).
Raso, V. and Stollar, B. D., "The Antibody–Enzyme Analogy. Characterization of Antibodies to Phosphopyriodoxyl-tyrosine Derivatives", *Biochemistry*, 14, 584–591 (1975).
Raso, V., and Stollar, B. D., "The Antibody–Enzyme Analogy. Comparison of Enzymes and Antibodies Specific For Phosphopyriodoxyltyrosine", *Biochemistry*, 14, 591–599 (1975) (cited on page 2 of present application).
Kohen, F. et al., "A Steroid Imunoassay Based On Antibody–Enhanced Hydrolysis Of A Steroid–Umbelliferone Conjugate", *FEBS Letters*, 100, 137–140 (1979).
Kohen et al. *FEBS Letters*, 104, 201 (1979).
Kohen, F. et al., "Nonradioisotopic Homogeneous Steroid Immunoassays", *J. Steroid Biochemistry*, 11, 161–167 (1979).
Kohen, F. et al., "Antibody–Enhanced Hydrolysis Of Steroid Esters", *Biochimica et Biophysica Acta*, 629, 328–337 (1980).
Kohen et al. "An Esterase–Like Activity of the Antibody–Combining Site?" *FEBS Letters*, 111, 427 (1980).

*Primary Examiner*—Charles L. Patterson, Jr.
*Attorney, Agent, or Firm*—Curtis, Morris & Safford; Barry Evans

[57] ABSTRACT

Process for producing an immunoproximity catalyst for a chemical reaction. Chemical reactions in which the immunoproximity catalyst can be used are also disclosed.

28 Claims, No Drawings

PRODUCTION OF IMMUNOPROXIMITY CATALYSTS

This application is a continuation of application Ser. No. 07/857,683, filed Mar. 25, 1992 which in turn is a continuation of application Ser. No. 07/092,230 filed Sep. 2, 12987, both now abandoned.

BACKGROUND OF THE INVENTION

1. Field of the Invention

This invention involves novel immunoproximity catalysts. The catalysts are derived from antibody molecules. The process includes selecting a hapten based on its relationship to a structure of a transition state complex of the selected reaction so that the hapten, upon attachment to a carrier protein and injection (with or without adjuvant) into an animal, elicits an immune response in which the desired antibody is produced. This antibody is modified by the specific, covalent attachment of the catalytic group involved in the selected reaction, yielding an immunoproximity catalyst which is a substrate-specific, antibody catalyst.

Catalysts are widely used in the chemical, pharmaceutical, and food processing industries. There is a continuing demand for new and/or improved catalysts. Improvements in specificity, selectivity, rate enhancement, and stability are desirable. Among known catalysts, enzymes— naturally occurring amino acid or RNA polymers—excel in terms of their ability to generate the highest possible reaction rates while maintaining high specificity. Simpler catalysts— based on organics or metals, for instance lack the specificity of enzymes but are often very stable. These simpler catalysts generally lack the stereo- and regiochemical control of reactions inherent in enzymes.

The success of enzymes as catalysts is attributed to their ability to fold (i.e. assume a spatial structure) so as to create specific binding pockets for the reactant and to place catalytically active groups in this pocket in close proximity to the scissle bond. These pockets are referred to as active sites.

A major obstacle to creating new enzymes—specific for a predetermined reactant and able to catalyze the desired reaction—is the rudimentary understanding of how proteins fold to form active sites. Minor alterations to an enzyme (and its catalytic properties) are possible via site directed mutagenesis. However, substitution of a single amino acid for another in a protein sequence can affect the folding and/or function of the molecule in large and unpredictable ways.

DESCRIPTION OF THE PRIOR ART

International Patent PCT/US84/01951; G. P. Royer (Advances In Catalysis 29, 197, 1980; R. A. Lerner (Advances in Immunology 36, 1, 1984); A. Tramontano et al (Proc. Nat. Acad. Sci., USA 83, 6736, 1986); Kohen et al (FEBS Letters 100, 137, 1979; 104,201, 1979; 111, 427, 1980; and Biochim. Biophys. Acta 629, 328, 1980); L. Slobin (Biochemistry 5, 2836, 1966); copending U.S. patent application Ser. No. 877,273, filed Jun. 23, 1986; V. Raso and B. D. Stollar (Biochemistry 14, 585, 591, 1975); A. Tramontano et al. (Science 234, 1566, 1986); and S. J. Pollack et al. (Science 234, 1570, 1986) are cited as representative of the state of the art.

SUMMARY OF THE INVENTION

The present invention comprises a process for producing an immunoproximity catalyst for a given chemical reaction. This process comprises identifying a reactant and a catalyst group for a chemical reaction, selecting a hapten which corresponds to the transition state complex of said reactant and said catalytic group, stimulating an immune response for production of antibodies by said hapten, isolating purified antibodies from said immune response which are specific for said hapten, selecting a converting hapten which corresponds to the transition state complex of said reactant and said catalytic group and is distinct from said hapten, modifying said purified antibodies by the covalent attachment of the catalytic group while said catalytic group is specifically bound in binding site of said purified antibodies as a part of said converting hapten yielding antibody-catalytic group complexes which are active for said chemical reaction; and isolating the antibody-catalytic group complexes which are active for said chemical reaction from said modification.

DESCRIPTION OF THE SPECIFIC EMBODIMENTS

The present invention comprises novel immunoproximity catalysts and a process for their production. The immunoproximity catalysts of the present invention are capable of acting both in vitro and in vivo, and in the human body itself. The catalysts of this invention are antibody molecules obtained by an immunization with a hapten that is similar to, but distinct from, the transition state complex for the reaction of the selected reactant and catalytic group and by subsequent modification with the converting hapten.

The relationship between the hapten and the reactant and catalytic group is the following: at least one chemical group in the hapten is identical in both its structure and orientation with a group in both the reactant and the catalytic group. This ensures that the hapten shares antigenic determinants with both the reactant and the catalytic group; i.e., the binding site of the antibody stimulated by hapten must interact with both the reactant and the catalytic group, the hapten must also differ structurally and chemically from the reactant and catalytic group in the vicinity of the nuclei and associated bonds to be altered in the reaction, e.g., one or more nuclei of higher valence is substituted for nuclei in either or both the reactant and the catalytic group; further, the substituted nuclei bear substituents, the role of which is to position complementary catalytic groups within the antibody binding surface and to create an additional cavity or cavities capable of enclosing cofactor molecules. The presence of one or more substantially similar groups or residues ensures that the hapten shares common antigenic determinants with both the reactant and the catalytic group. This in turn, ensures that the antibody will "recognize" the reactant in a selective manner and position the bound catalytic group for efficient catalysis. On the other hand, the hapten differs structurally and chemically from the reactant and catalytic group in the vicinity of the bonds to be altered in the reaction. Differences include substituting a nucleus of higher valency for one or more such nuclei in both the reactant and the catalytic group. In addition, residues appended from these substituted nuclei are so oriented as to induce additional, complementary groups or pockets for co-factor binding in the antibody that promote catalysis. The presence of these additional groups in the antibody binding surface increases the efficiency of the catalytic group and allows larger rate enhancements to be realized. Finally, the hapten differs from the catalytic group in the vicinity of the covalent bond to be formed with the antibody. This residue is identical to or of similar bulk and orientation to the corresponding residue in the catalytic group, i.e., it is substantially similar. However, when a photoactivatable crosslinker is to be used in the catalytic group, the corresponding group in the hapten is an unreactive analog of the crosslinker and when an electrophile group is to be used in the catalytic group, the corresponding group in the hapten is a charged analog to induce a positioned, reactive nucleophile in the antibody binding surface.

The purified, specific antibody obtained in an immune response to said hapten is subsequently modified by reaction with the converting hapten. The converting hapten is similar to, but distinct from, the hapten. The relationship is as follows: the converting hapten is identical to the hapten with the following exceptions—1) The actual catalytic group is used in the converting hapten instead of the analog used in the hapten; 2) No additional residues are appended to any of nuclei in the vicinity of the bonds to be altered during the reaction—as is the case for the hapten; and 3) The nucleus at the reaction center, i.e., the nucleus in the hapten substrate analog to which the hapten catalytic group analog is bound—may be altered to suit the stability requirements of the converting hapten. Upon modification by the converting hapten, the antibody acquires catalytic power in addition to its normal and highly selective binding capacity.

The immunoproximity catalysts of the process, whether obtained polyclonally or monoclonally, are well-folded, stable proteins by virtue of their derivation in an immune response. This invention thus circumvents present uncertainties concerning folding of proteins of novel sequence. The process of immunization using the haptens of this invention to produce antibodies is defined as active immunization.

The said proteins of this invention, upon modification, include a novel class of antibodies that are chemically reactive against their target antigenic species (the reactant), in that they catalyze cleavage of bonds in these target molecules—in the manner of an enzyme—instead of passively binding antigens.

Conversion of bimolecular reactions to unimolecular reactions result in very large increases in the rate of reaction. The immunoproximity catalysts of this invention will serve this function as well as aligning the reactant and catalytic group to maximize the rate of reaction. The types of reaction catalyzed are limited only by the type of catalytic group which can be attached to said antibody. These catalytic groups include general acid-base, nucleophilic, electrophilic, and metal catalysts. It is also possible to use more than one catalytic group. Two large classes of reactions to which the catalysts of this invention are applicable are hydrolysis reactions and oxidation-reduction reactions.

Definitions

Reactant—the molecule to be converted chemically in a particular chemical transformation to product(s).

Catalytic Group—the catalytically active moiety which is covalently bound to the elicited antibody molecule while occupying its specificity site on the antibody molecule.

Cofactor—an additional molecule(s) participating in the reaction, including $H_2O$ in hydrolytic reactions.

Linker Group—the moiety included in the catalytic group used to form the covalent attachment of the catalytic group to the elicited antibody.

Hapten—a molecule attached covalently to a carrier protein that elicits an antibody response directed towards itself.

Antigen—the combined hapten-carrier complex used to stimulate the immune response.

Converting Hapten—the molecule used to attach the catalytic group to the elicited antibody while it is occupying its specificity pocket in the antibody binding site.

The selected reactant and catalytic group are represented in the transition state complex as a tetrapartite molecule

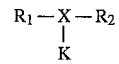
FORMULA I wherein $R_1$ and $R_2$, which do not participate in the catalytic events, represent the residual chemical groups in the reactant after the reaction site has been designated as X and the catalytic group as K. X represents the reaction site which comprises the portion of the reactant altered during the catalytic reaction. K represents the catalytic group.

The haptens of this invention corresponding to the reactant-catalytic group complex are molecules selected, or chemically synthesized, having the structure

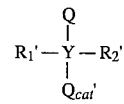
FORMULA II wherein $R'_1$ and $R'_2$ are substantially similar to $R_1$ and $R_2$ of the reactant (except for possible addition $R_1'$ and $R_2'$ of a group), as shown in Table 1, which links the hapten to the carrier and Y represents nuclei and associated bonds which comprise the portion of the hapten molecule corresponding to the X region of the reactant and:

(1) X and Y are related to each other in that Y has a higher valence state and one or more bonds than X. Table 2 represents this relationship between X and Y.

(2) Q represents one (or more) substituents as shown in Table 3 bound to Y in (1) such that:
  (a) Q contains a negative charge(s) when catalysis requires a positive charge(s) in the active surface of the antibody catalyst, and vice-versa.
  (b) Q is polar and neutral when catalysis requires a polar component in said active surface.
  (c) Q is non-polar (or hydrophobic) when catalysis requires a non-polar component in said active surface.
  (d) When one or more cofactors are involved in the reaction, Q is selected to be a substituent of substantial bulk so as to create a cavity in the active surface to allow for one or more of said co-factors to bind, including $H_2O$ in the case of hydrolytic reaction.
  (e) Q can contain in addition a group as shown in Table 1 capable of linking the hapten to carrier, in case attachment at the Y region is desired.

(3) $Q'_{cat}$ is synthesized to be a molecule of the type

K'–L'  FORMULA III wherein K' represents a catalytic group analog as shown in Table 4 and L' represents an unreactive linker analog of L, the linker group. L' induces the presence of a group in the antibody binding surface which is reactive with L. Both L and L' are shown in Table 5.

When several possible substituents are appropriate for the catalytic process of this invention, prefered choices are selected as those which minimize differences in binding affinity between the reactant and the hapten. These relative affinities are tabulated in the treatise by Pressman and Grossberg, The Structural Basis of Antibody Specificity, Benjamin, N.Y., 1969, for example. These data are used to ensure a sufficient degree of similarity in binding of reactant and hapten such that both molecules will be bound by the immunoproximity catalysts resulting from this invention.

4) The remaining groups $R'_1$ and $R'_2$ so linked to Y are selected to be identical or of similar size and charge to corresponding groups in X, i.e., they are substantially similar.

The Formulas I–III and the algorithm set forth above define the correspondence between the hapten and reactant in this invention. That is the hapten is selected, or synthesized chemically, to correspond to the reactant according to above Formulas I–III. The identity of X in some important reactions is illustrated in Table 6.

The converting haptens of this invention corresponding to the hapten are molecules selected, or synthesized chemically, having the structure

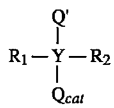

FORMULA IV wherein $R_1$ and $R_2$ are identical to $R_1$ and $R_2$ of the reactant, Y is identical to Y of the hapten, $Q_{cat}$ contains the active catalytic group, K as well as the linker group, L, and;

(1) Q' may be the same group(s) as in the hapten or, to decrease the binding affinity of 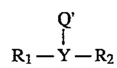 for the elicited antibody may be hydrogen.

(2) $Q_{cat}$ is a molecule chemically synthesized, or selected, to be a molecule of the type

K–L FORMULA V wherein K is the selected catalytic group as shown in Table 4 and L is the linker group as shown in Table 5, covalently bound to the selected catalytic group, used to permanently, covalently bind the selected catalytic group to the elicited antibody. When L is selected to contain a photoactivatable crosslinking group, L' is an unreactive analog of the crosslinking group. When L is selected to contain an electrophile group, L' is a charged unreactive analog which induces a positioned, reactive nucleophile in the antibody binding surface.

Formulas IV and V and the accompanying algorithm define the relationship of the reactant and hapten to the converting hapten. That is the converting hapten is chemically synthesized or selected to correspond to the reactant and hapten according to above Formulas IV and V.

The converting hapten is incubated with the elicited antibody. The converting hapten reacts with said antibody, or is caused to react, the bond between the Y group and the $Q_{cat}$ group is broken (for instance with mild acid or mild base) in such a way that the integrity of the antibody molecule is preserved, and th 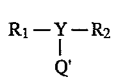 from the antibody's binding site. This results in a fully catalytic antibody.

TABLE 1

Partial List of Linkage Groups For Attachment Of Haptens To Carrier Proteins

| Group | Bond To Carrier |
|---|---|
| $-(CH_2)$*n $-NH_2$ | amide |
| $CO_2$ | ester, amide |
| OH | ester |
| SH | disulfide |

*n can be varied to maximize attachment and antigenicity. Groups other than $-CH_2-$ ($-OC-CH_2NH$ - for example) can be used as spacers.

TABLE 2

Some Substitutions of Higher Valence Useful for Nuclei In the X Region Of The Reactant

| Substrate: Nuclei in X | Hapten: Nuclei in Y |
|---|---|
| O,S (oxygen, sulfur) | N or C (nitrogen or carbon) |
| N (nitrogen) | C (carbon) |
| C (carbon) | P (phosphorus) |

TABLE 3

Some Useful Substituents, Q, For Attachment In The Y Region Of Haptens

| | |
|---|---|
| A) | For introducing a (+) charge(s) in the antibody binding surface<br>$-CO_{2(-)}$<br>$-PO_{4(-2)}$<br>$-SO_{4(-2)}$<br>$-SO_{3(-2)}$ |
| B) | For introducing a (–) charge(s) in the antibody binding surface<br>$-NH_{3(+)}$<br>$-NRH_{2(+)}$<br>$-NR_2H^{(+)}$<br>$-NR_{3(+)}$<br>$-SR_{2(+)}$<br>R = any stable alkyl or aryl group - all R groups need not be identical. |
| C) | To replace $-OH$ in the reactant<br>$-Cl$<br>$-Br$<br>$-CF_3$<br>$=O$ |
| D) | To create polar environments<br>$-NO_2$<br><br>$-N-(CH_2F)_2$<br>$-Cl$<br>$-Br$<br>$-CF_3$<br>$-SH$<br>$-OH$<br> 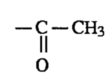 |
| E) | To create non-polar environments<br> |

TABLE 3-continued

Some Useful Substituents, Q, For Attachment In The Y Region Of Haptens

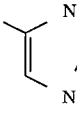

—CH₃
—CH—(CH₃)₂

F) To provide a cavity for H₂O
—CO₂⁽⁻⁾
—NH₂/NH₃⁽⁺⁾
—NO₂

TABLE 4

Some Small Molecule Catalysts, K, and Stable Analogs, K', Useful For Converting Hapten and Hapten

| Catalytic Group, K | Analog, K' |
|---|---|
| 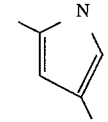 | 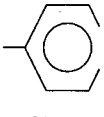 |
| 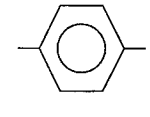 | 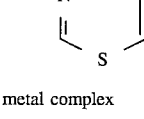 |
| —CO₂H | $-\overset{O}{\underset{\|}{C}}-CH_2-$ |
| —H₂PO₃ | $-O-\overset{O}{\underset{\|}{P}}-CH_2-$ $\quad\underset{O^-}{\|}$ |
| —NH₂<br>—OH<br><br>—SH | —CH₂—<br>—NH₂—<br>—CH₂—<br>—NH₂—<br>—CH₂— |
| 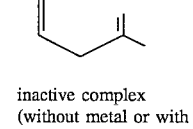<br>metal complex | <br>inactive complex (without metal or with incorrect metal) |
|  |  |
|  |  |

TABLE 4-continued

Some Small Molecule Catalysts, K, and Stable Analogs, K', Useful For Converting Hapten and Hapten

| Catalytic Group, K | Analog, K' |
|---|---|
|  | 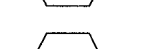 |
| 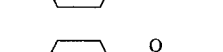 |  |
| $-\overset{O}{\underset{\|}{C}}\underset{H}{\overset{\|}{N}}-OH$ | $-CH_2N\overset{O}{\underset{\|}{H}}C-$ |

TABLE 5

Some Groups, L, Used To Link The Catalytic Group, K, To Antibody And Their Corresponding Groups, L'; For Use In The Hapten

| Linker Group, L | Linker Group Analog, L' |
|---|---|
|  | |
| —(CH₂)*ₙ—⌬—N₃ (with NO₂) | —(CH₂)*ₙ—⌬—CH₂CN (with NO₂) |
| —(CH₂)ₙ—C(O)—C(CF₃)=N₂ | —(CH₂)ₙ—C(O)—C(CH₃)—CN |
| —(CH₂)ₙ—⌬—CH(N=N ring) | —(CH₂)ₙ—⌬—CH(CH₂ ring) |
| (CH₂)ₙ—CO₂⁽⁻⁾ | —(CH₂)ₙ—C(O)—CH₂Cl |
| (CH₂)ₙ—PO₄⁽⁻²⁾ | (CH₂)ₙ—CH—CH₂ (epoxide) |
| (CH₂)ₙ—NH₃⁺ | (CH₂)ₙ—C(O)—CH₂Cl |
|  | (CH₂)ₙ—CH—CH₂ (epoxide) |
| (CH₂)ₙ—C(O)—CH₂Cl | (CH₂)ₙ—PO₄⁽⁻²⁾ |

*ₙ can be varied to maximize attachment and antigenicity. Groups other than —CH₂—(OC—CH₂NH - for example) can be used as spacers.

TABLE 6

The Identity Of X In Some Important Reactions

| | Reactant | X |
|---|---|---|
| A) General Ester Hydrolysis $$R_1-\overset{O}{\underset{\|}{C}}-O-R_2 \xrightarrow{H_2O} R_1-\overset{O}{\underset{\|}{C}}-OH + HO-R_2$$ | $R_1-\overset{O}{\underset{\|}{C}}-O-R_2$ | $-\overset{O}{\underset{\|}{C}}-O-$ |
| B) General Amide Hydrolysis $$R_1-\overset{O}{\underset{\|}{C}}-NH-R_2 \xrightarrow{H_2O} R_1-\overset{O}{\underset{\|}{C}}-OH + H_2N-R_2$$ | $R_1-\overset{O}{\underset{\|}{C}}-NH-R_2$ | $-\overset{O}{\underset{\|}{C}}-NH-$ |
| C) General Phosphodiester Hydrolysis $$R_1-O-\underset{OH}{\overset{O}{\underset{\|}{P}}}-O-\underset{\|}{\overset{\|}{C}}-R_2 \xrightarrow{H_2O} R_1-O-\underset{OH}{\overset{O}{\underset{\|}{P}}}-OH + HO-\underset{\|}{\overset{\|}{C}}-R_2$$ | $R_1-O-\underset{OH}{\overset{O}{\underset{\|}{P}}}-O-\underset{\|}{\overset{\|}{C}}-R_2$ | $-\underset{\|}{\overset{O}{\underset{\|}{P}}}-O-\underset{\|}{\overset{\|}{C}}$ |
| D) General Carbamate Hydrolysis $$R_1-\underset{R_1}{N}-\overset{O}{\underset{\|}{C}}-O-R_2 \xrightarrow{H_2O} R_1-\underset{R_1}{N}-\overset{O}{\underset{\|}{C}}-OH + HO-R_2$$ | $R_1-\underset{R_1}{N}-\overset{O}{\underset{\|}{C}}-O-R_2$ | $-\overset{O}{\underset{\|}{C}}-O-$ |
| E) General Acetal Hydrolysis $$R_1-O-\underset{R_1}{\overset{R_2}{\underset{\|}{C}}}-O-R_2 \xrightarrow{H_2O} R_1-OH + HO-\underset{R_1}{\overset{R_2}{\underset{\|}{C}}}-O-R_2$$ | $R_1-O-\underset{R_1}{\overset{R_2}{\underset{\|}{C}}}-O-R_2$ | $O-\underset{\|}{\overset{\|}{C}}-$ |

TABLE 7

The Relationship Between Reactant - X, Catalytic Group K, $R_1$ & $R_2$; Hapten - Y, $Q_{cat}$, $R_1'$, & $R_2'$; And Converting Hapten Y - $Q_{cat}$, $R_1$, & $R_2$ For Some Selected Reactions A) Reaction: p-Nitrophenylbutyrate hydrolysis

| reactant | X | K | $R_1$ | $R_2$ |
|---|---|---|---|---|
| $O_2N-\phenyl-O-C(=O)-CH_2CH_2CH_3 \xrightarrow{H_2O} O_2N-\phenyl-OH + HO-C(=O)-CH_2CH_2CH_3$ | $-O-C(=O)-$ | imidazole (N⌒N-CH₃) | $O_2N-\phenyl-$ | $-(CH_2)_2-CH_3$ |

| hapten | Y–Q | $Q_{cat}$ | $R_1'$ | Rhd 2' |
|---|---|---|---|---|
| $O_2N-\phenyl-O-P(=O)(-(CH_2)_2-SH)-$ [pyrrole with $(CH_2)_3$ substituent bearing $NO_2$/$CH_2CN$ phenyl] | $-O-P(=O)-$ | [nitro-cyanomethyl-phenyl-(CH₂)₃-pyrrole] | $O_2N-\phenyl-$ | $-(CH_2)_2-SH$ |

| converting hapten | Y–Q' | $Q_{cat}$ | $R_1$ | $R_2$ |
|---|---|---|---|---|
| $O_2N-\phenyl-O-P(=O)(CH_2-)(-(CH_2)_2-CH_3)$ [imidazole with $(CH_2)_3$ substituent bearing $NO_2$/$N_3$ phenyl] | $-CH_2-P(=O)-$ | [nitro-azido-phenyl-(CH₂)₃-imidazole] | $O_2N-\phenyl-$ | $-(CH_2)_2-CH_3$ |

B) Reaction: tryptophonyl leucine hydrolysis

TABLE 7-continued

The Relationship Between Reactant - X, Catalytic Group K, R₁, & R₂; Hapten - Y, Q_{cat}, R₁', & R₂'; And Converting Hapten Y - Q_{cat}, R₁, & R₂ For Some Selected Reactions

| reactant | X | K | R₁ | R₂ |
|---|---|---|---|---|
| 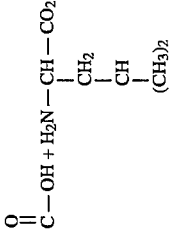 | $-C(=O)-NH-$ | 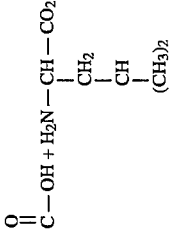 | 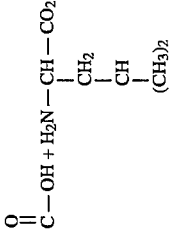 | $\begin{array}{l}-CHCO_2H \\ \phantom{-}|\\ \phantom{-}CH_2\\ \phantom{-}|\\ \phantom{-}CH\\ \phantom{-}(CH_3)_2\end{array}$ |

| hapten | Y—Q | Q_{cat} | R₁' | R₂' |
|---|---|---|---|---|
|  | $\begin{array}{l}O\ CO_2H\\ \|\!\!\|\ \ \|\\ -P-C-\\ \|\ \ \ \|\\ \phantom{-}\ \ H\end{array}$ |  |  | $\begin{array}{l}(CH_2)_2SH\\ -C-CO_2H\\ \phantom{-}|\\ CH_2CH-(CH_3)_2\end{array}$ |

| converting hapten | Y—Q' | Q_{cat} | R₁ | R₂ |
|---|---|---|---|---|

TABLE 7-continued

The Relationship Between Reactant - X, Catalytic
Group K, R$_1$ & R$_2$; Hapten - Y, Q$_{cat}$,
R$_1$', & R$_2$'; And Converting Hapten Y - Q$_{cat}$,
R$_1$, & R$_2$ For Some Selected Reactions C) Reaction: Removal of N-terminal acetyl group from serine $$CH_3C(=O)-NHCH(CH_2OH)-CO_2H + H_2O \rightarrow CH_3C(=O)-OH + H_2N-CH(CH_2OH)-CO_2H$$

| | reactant | X | K | R$_1$ | R$_2$ |
|---|---|---|---|---|---|
| | CH$_3$C(=O)—NHCH(CH$_2$OH)—CO$_2$H | —C(=O)—NH— | 4-aminophenyl— | CH$_3$— | —CH(CO$_2$H)(CH$_2$OH) |

| | hapten | Y—Q | Q$_{cat}$' | R$_1$' | R$_2$' |
|---|---|---|---|---|---|
| | phosphonate analog with CH$_2$OH, CO$_2$H substituents | —P(=O)(CH(CO$_2$H)(CH$_2$OH))— | 4-CH$_2$-phenyl-(CH$_2$)$_3$—PO$_4^{(-2)}$ | —CH$_3$ | —C(CH$_2$)$_3$SH(CO$_2$H)(CH$_2$OH) |

| | converting hapten | Y—Q' | Q$_{cat}$ | R$_1$ | R$_2$ |
|---|---|---|---|---|---|
| | —(CH$_2$)$_3$—PO$_4^{(-2)}$ | | | | |

TABLE 7-continued

The Relationship Between Reactant - X, Catalytic Group K, $R_1$ & $R_2$; Hapten - Y, $Q_{cat}$, $R_1'$, & $R_2'$; And Converting Hapten Y - $Q_{cat}$, $R_1$, & $R_2$ For Some Selected Reactions

| | | | |
|---|---|---|---|
| $CH_3-\overset{O}{\overset{\|}{P}}-CH_2-\underset{\underset{CH_2OH}{\|}}{CHCO_2H}$ | $-\overset{O}{\overset{\|}{P}}-CH_2-$ | $-CH_3$ | $-\underset{\underset{CH_2OH}{\|}}{CHCO_2H}$ |
| $-\overset{\|}{NH}-\underset{}{\underset{}{\bigcirc}}-(CH_2)_3-\overset{O}{\overset{\|}{C}}CH_2Cl$ | $-NH-\underset{}{\underset{}{\bigcirc}}-(CH_2)_3-\overset{O}{\overset{\|}{C}}CH_2Cl$ | | |

D) Reaction: Carbaryl hydrolysis:

reactant: naphthyl-$O-\overset{O}{\overset{\|}{C}}NHCH_3$  $\xrightarrow{H_2O}$ naphthyl-$OH$ + $HO-\overset{O}{\overset{\|}{C}}NHCH_3$ hapten: naphthyl-$O-\overset{O}{\overset{\|}{C}}NH-CH_3$

| X | K | $R_1$ | $R_2$ |
|---|---|---|---|
| $-O-\overset{O}{\overset{\|}{C}}-$ | imidazole | naphthyl | $-NHCH_3$ |

| Y—Q | $Q_{cat}$ | $R_1'$ | $R_2'$ |
|---|---|---|---|

TABLE 7-continued

The Relationship Between Reactant - X, Catalytic Group K, $R_1$, & $R_2$; Hapten - Y, $Q_{cat}$, $R_1'$, & $R_2'$; And Converting Hapten Y - $Q_{cat'}$, $R_1$, & $R_2$ For Some Selected Reactions

| | | | | |
|---|---|---|---|---|
| converting hapten | Y — Q' | $Q_{cat}$ | $R_1$ | Rhd 2 |

E) Reaction of Carbobenzoxy protecting group from lysine:

| | | | | |
|---|---|---|---|---|
| reactant | X | K | $R_1$ | $R_2$ |
| hapten | Y — Q | $Q_{cat}'$ | $R_1'$ | $R_2'$ |

TABLE 7-continued
The Relationship Between Reactant - X, Catalytic Group K, R$_1$ & R$_2$; Hapten - Y, Q$_{cat}$, R$_1$', & R$_2$'; And Converting Hapten Y - Q$_{cat}$, R$_1$, & R$_2$ For Some Selected Reactions
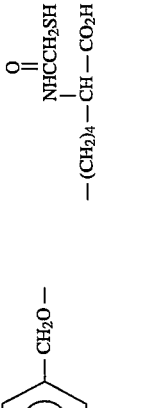
F) Reaction: Benzocaine hydrolysis
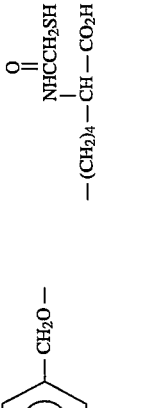
| | X | K | R$_1$ | R$_2$ |
|---|---|---|---|---|
| reactant | —C(=O)—O— | —CO$_2^{(-)}$ | H$_2$N—C$_6$H$_4$— | —CH$_2$CH$_3$ |
| | Y—Q | Qhd cat' | R$_1$' | R$_2$' |
| hapten | | | | |

TABLE 7-continued

The Relationship Between Reactant - X, Catalytic Group K, $R_1$ & $R_2$; Hapten - Y, $Q_{cat}$, $R_1'$, & $R_2'$; And Converting Hapten Y - $Q_{cat}$, $R_1$, & $R_2$ For Some Selected Reactions

[Chemical structures for converting hapten, Y—Q', $Q_{cat}$, $R_1$, $R_2$ columns showing phosphorus-containing aromatic compounds with $H_2N$, $HSCH_2CH_2$ substituents, and diazirine groups]

G) Reaction: Mephenesin carbamate hydrolysis reactant: $CH_3$-phenyl-$OCH_2CHCH_2O-\overset{O}{\overset{\|}{C}}-CNH_2$ with OH group, + $H_2O$ → $CH_3$-phenyl-$OCH_2CHCH_2OH$ with OH + $HO-CNH_2$

| X | K | Y—Q | Qhd cat' | $R_1$ | $R_2$ |
|---|---|---|---|---|---|
| $-O-\overset{O}{\overset{\|}{C}}-$ | [methylimidazole structure] | | | $CH_3$-phenyl with OH | $-NH_2$ | hapten: $CH_3$-phenyl-$OCH_2CHCH_2OCNH_2$ with OH, $R_1'$: $CH_3$-phenyl-$OCH_2CHCH_2-$ with OH, $R_2'$

TABLE 7-continued

The Relationship Between Reactant - X, Catalytic Group K, $R_1$, & $R_2$; Hapten - Y, $Q_{cat}$, $R_1$, & $R_2$; And Converting Hapten Y - $Q_{cat'}$ $R_1$, & $R_2$ For Some Selected Reactions

| | | | | |
|---|---|---|---|---|
| converting hapten | Y — Q' | $Q_{cat}$ | $R_1$ | $R_2$ |

H) Reaction: Phenacemide hydrolysis

| | X | K | $R_1$ | $R_2$ |
|---|---|---|---|---|
| reactant | | | | |
| hapten | Y — Q | Qhd cat' | $R_1'$ | $R_2'$ |

TABLE 7-continued
The Relationship Between Reactant - X, Catalytic Group K, $R_1$ & $R_2$; Hapten - Y, $Q_{cat}$, $R_1'$, & $R_2'$; And Converting Hapten Y - $Q_{cat'}$, $R_1$, & $R_2$ For Some Selected Reactions
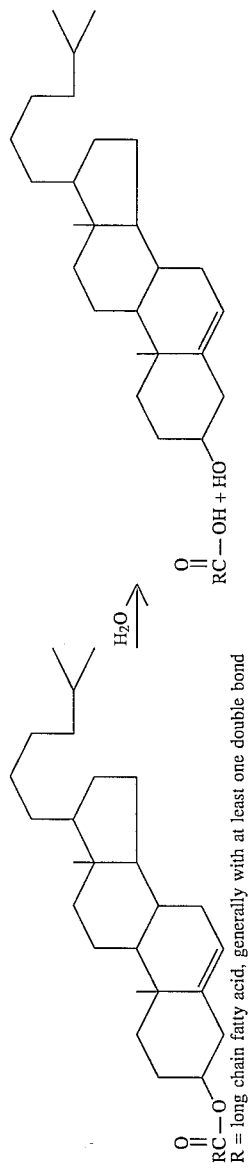
I) Reaction: Cholesterol ester hydrolysis
R = long chain fatty acid, generally with at least one double bond

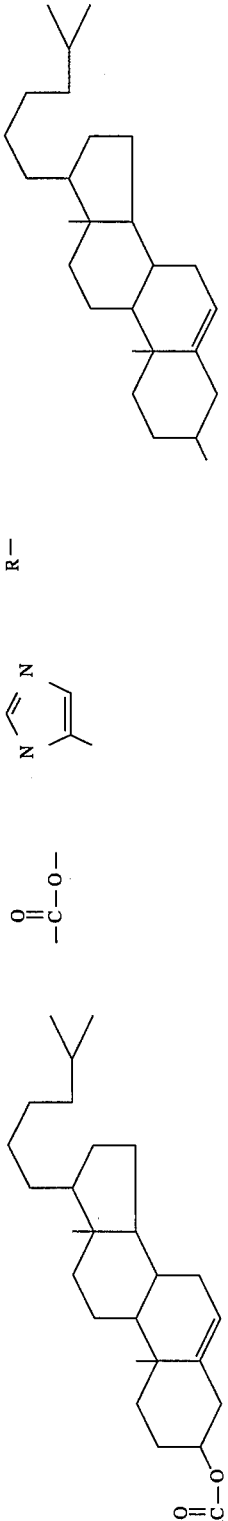

The process of this invention comprises selecting or synthesizing a hapten according to the algorithm set forth above, preferably covalently linking said hapten(s) to carrier species such as keyhole limpet hemocyanin or similar proteins in standard use for this purpose via the linking residue provided for above, and injecting the complex into an appropriate animal as antigen to stimulate the immune response. Following a time sufficient for said response to develop, the animal is bled, serum is extracted and fractionated (preferably over a column containing covalently linked hapten) to remove non-specific antibodies including these responsive to carrier alone, according to standard procedures. This purified antibody fraction is then incubated with the analogous converting hapten (selected or synthesized according to the algorithm for converting haptens set forth above). According to the type of converting hapten used, the purified antibody— converting hapten complex is reacted, allowed to react, or simply purified if reaction is spontaneous. The reacted complex is then treated with either mild acid or mild base— preserving the structure of the antibody—extensively dialyzed against buffer, and fractionated (preferably over a column containing covalently linked hapten). This purified preparation is assayed by conventional means for catalytic activity that can be inhibited by a hapten analog which does not contain the $Q'_{cat}$ group, but not by unrelated molecules of comparable size or structure.

Such immunoproximity catalysts, as will be apparent to those skilled in the art, are useful as catalysts for chemical reactions of industrial importance; e.g. as active ingredients in detergents, for degrading carbohydrates in the conversion of starch or cellulose to sugar, for cheese production, and for treatment of human diseases.

Other areas that immunoproximity catalysts are useful for are in organic synthesis and site specific cleavage of biopolymers. Also, the inactivation of drugs or toxins.

In organic synthesis they are particularly useful in synthesis of chiral compounds, the selective reaction of one of a number of similar bonds, and catalysis of one of a mixture of compounds. Traditional catalysts tend to lack stereospecificity, selectivity, and/or substrate specificity. Besides overcoming these problems, immunoproximity catalysts offer significant rate enhancements and milder reaction conditions than traditional catalysts.

Immunoproximity catalysts also are of considerable use when protective groups are employed in synthesis. An immunoproximity catalyst can remove a protective group without altering the reactant in any other respect.

As site-specific cleavage catalysts, immunoproximity catalysts are useful from protein sequencing to anti-cancer therapy. To facilitate protein sequencing, for example, an immunoproximity catalyst an be produced to catalyze the hydrolysis of N-terminal formyl or acetyl groups, and can be produced to catalyze the cleavage of proteins at the rare amino acids such as tryptophan, methionine, or histidine.

The compounds used in the production of the immunoproximity catalysts as shown in the above tables are offered by way of illustration and not by way of limitation. These compounds can be prepared using the conventional techniques of organic synthesis.

It is the intent of the inventors to commercially develop the immunoproximity catalysts described and claimed herein under the trademark Immunozyme.

What is claimed is:

1. A process for producing an immunoproximity catalyst for a chemical reaction which comprises the steps of:

(1) selecting a hapten for a transition state complex of a reactant and a selected catalytic group for said reaction, which hapten shares antigenic determinants with said reactant and said catalytic group, and which hapten when covalently bound to a carrier protein is capable of eliciting an antibody which selectively binds to said hapten and to a converting hapten;

(2) eliciting an immune response for production of antibodies by said hapten;

(3) isolating antibodies from said immune response which are specific for said hapten;

(4) selecting a converting hapten for the transition state complex of said reactant and said catalytic group, which converting hapten shares antigenic determinants with said reactant and which further includes said catalytic group attached thereto;

(5) modifying said isolated antibodies by the transfer of said catalytic group from said converting hapten to binding sites of said isolated antibodies, said catalytic group being specifically and covalently bound in the binding sites of said isolated antibodies to form covalent antibody-catalytic group complexes which are active for said chemical reaction; and (6) isolating said antibody-catalytic group complexes which are active for said chemical reaction.

2. The process of claim 1 wherein the reactant is represented by the formula $R_1-X-R_2$, the complex of the reactant and the selected catalytic group is represented by the formula $$R_1 - X - R_2, \\ \phantom{R_1 - }| \\ \phantom{R_1 - }K$$

the hapten for a transition state of the complex of the reactant and the selected catalytic group is represented by the formula $$\phantom{R'_1 - }Q \\ \phantom{R'_1 - }| \\ R'_1 - Y - R'_2, \\ \phantom{R'_1 - }| \\ \phantom{R'_1 - }Q'_{cat}$$

and the converting hapten is represented by the formula $$\phantom{R_1 - }Q' \\ \phantom{R_1 - }| \\ R_1 - Y - R_2 \\ \phantom{R_1 - }| \\ \phantom{R_1 - }Q_{cat}$$

wherein X is a portion of the reactant altered in the reaction, K the catalytic group, and Y is the reaction site which comprises the analogous portion of the hapten molecule and the converting hapten molecule with respect to X, and X and Y are analogous to each other in that Y represents X in its transition state, and wherein Q and Q' represent one or more substituents bonded to Y in the hapten and converting hapten, respectively, and wherein $Q_{cat}$ is

K–L wherein L represents the linker group which is the remainder of the molecule which is used to form a permanent bond between the catalytic group and the antibody molecule, and wherein $Q'_{cat}$ is

K'–L' wherein K' represents an unreactive analog of K which will form a stable bond with Y, and wherein L' is an unreactive analog of L which induces the presence of a group in the antibody binding surface which is reactive with L and wherein $R_1$, $R_2$, and $R'_1$ and $R'_2$ represent the residual chemical groups of the reactant, hapten, and converting hapten which do not participate in the catalytic events, and $R_1$ and $R'_1$ and $R_2$ and $R'_2$ are, respectively, substantially similar to each other, said $R'_1$ and $R'_2$ being of similar size and charge to $R_1$ and $R_2$, respectively.

3. The process of claim 2 wherein L contains a photoactivatable crosslinking group and L' is an unreactive analog of said crosslinking group.

4. The process of claim 2 wherein X is 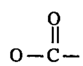 wherein Y–Q of the hapten is 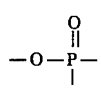 wherein K is 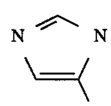 wherein $Q'_{cat}$ is 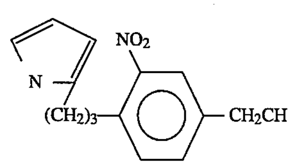 wherein Y–Q' of the converting hapten is 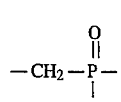 wherein K' is 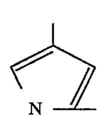 wherein L is 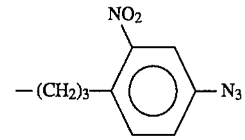 and wherein L' is 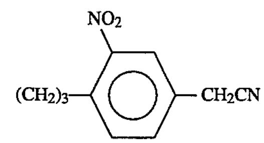 5. The process of claim 2 wherein Q is selected from the group consisting of (a) a positively charged substituent (b) a negatively charged substituent (c) a polar substituent (d) a nonpolar substituent, and (e) a substituent having substantial bulk.

6. The process of claim 2 wherein Q' is selected from the group consisting of (a) a positively charged substituent, (b) a negatively charged substituent, (c) a polar substituent, (d) a non-polar substituent, (e) a substituent having substantial bulk and (f) hydrogen.

7. The process of claim 2 wherein L contains a photoactivatable crosslinking group and L' is an unreactive analog of said crosslinking group.

8. The process of claim 2 wherein L contains an electrophilic group and L' is a charged unreactive analog which induces a reactive nucleophile in the antibody binding surface able to enhance catalytic activity.

9. The process of claim 2 wherein X is a moiety within which there is an element selected from the group consisting of oxygen or sulfur, and Y is a moiety within which there is an element selected from the group consisting of nitrogen or carbon.

10. The process of claim 2 wherein X is a moiety within which there is nitrogen, and Y is a moiety within which there is carbon.

11. The process of claim 2 wherein X is a moiety within which there is carbon, and Y is a moiety within which there is phosphorus.

12. The process of claim 5 wherein Q is a substituent having a positive charge.

13. The process of claim 12 wherein said substituent is $—NH_3^{(+)}$.

14. The process of claim 5 wherein Q is a substituent having a negative charge, said substituent selected from the group consisting of $—CO_2^{(-)}$, $—PO_4^{(-2)}$, $—SO_4^{(-2)}$, $—SO_3^{(-2)}$.

15. The process of claim 5 wherein Q is a polar substituent selected from the group consisting of $—NO_2$, 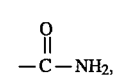 $—N—(CH_2F)_2$, —Cl, —Br, $—CF_3$, —SH, 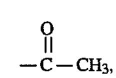 and —OH.

16. The process of claim 5 wherein Q is a non-polar substituent selected from the group consisting of —C(CH$_3$)$_3$, —CH$_3$, —CH(CH$_3$)$_2$

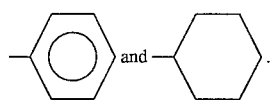

17. The process of claim 5 wherein Q is a substituent having substantial bulk selected from the group consisting of —CO$_2^{(-)}$, —NH$_2$, —NH$_3^{(+)}$, and —NO$_2$.

18. The process of claim 2 wherein K is selected from the group consisting of

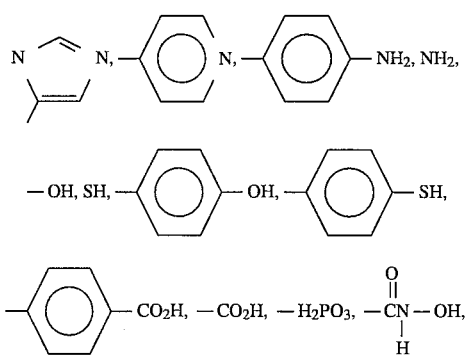

and a chelate containing an element is selected from the group consisting of Fe, Co, Cu, Pb, Ti, Al, Pd, B, and Mg.

19. The process of claim 2 wherein K' is selected from the group consisting of

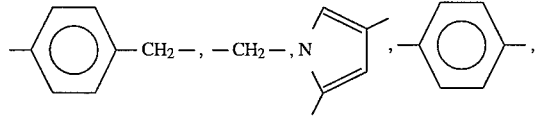

-continued

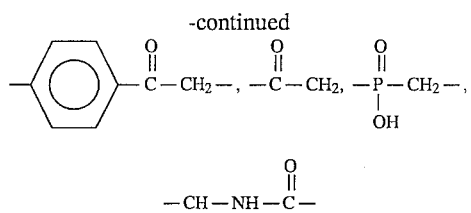

and an uncomplexed chelate.

20. The process of claim 1 wherein the catalytic group includes an acid-base catalyst.

21. The process of claim 1 wherein the catalytic group includes a nucleophilic catalyst.

22. The process of claim 1 wherein the catalytic group includes an oxidation-reduction catalyst.

23. The process of claim 1 wherein the chemical reaction is hydrolysis of polydeoxynucleotides or polyribonucleotides containing a specified sequence of nucleic acids.

24. The process of claim 1 wherein the chemical reaction is hydrolysis of protein molecules containing a specified sequence of amino acids.

25. The process of claim 1 wherein the chemical reaction is hydrolysis of an acetal bond.

26. The process of claim 25 wherein the acetal bond is in a polysaccharide containing a specific sequence of sugars.

27. The process of any one of claims 1, 20, 21 or 22 wherein the chemical reaction is hydrolysis of a drug having a bond selected from the group consisting of an ester, amide, and acetal bond.

28. The process of any one of claims 20, 21 or 22 wherein the chemical reaction is a hydrolysis selected from the group consisting of: hydrolysis of polydeoxynucleotides or polyribonucleotides containing a specified sequence of nucleic acids; hydrolysis of protein molecules containing a specified sequence of amino acids; and hydrolysis of an acetal bond.

* * * * *